(12) United States Patent
Gorenstein et al.

(10) Patent No.: US 8,511,140 B2
(45) Date of Patent: Aug. 20, 2013

(54) BASELINE MODELING IN CHROMATOGRAPHY

(75) Inventors: Marc V. Gorenstein, Needham, MA (US); Anthony C. Gilby, Foxborough, MA (US)

(73) Assignee: Waters Technologies Corporation, Milford, MA (US)

( * ) Notice: Subject to any disclaimer, the term of this patent is extended or adjusted under 35 U.S.C. 154(b) by 793 days.

(21) Appl. No.: 12/090,111

(22) PCT Filed: Oct. 25, 2006

(86) PCT No.: PCT/US2006/060217
§ 371 (c)(1),
(2), (4) Date: Jul. 22, 2010

(87) PCT Pub. No.: WO2007/051117
PCT Pub. Date: May 3, 2007

(65) Prior Publication Data
US 2010/0280811 A1    Nov. 4, 2010

Related U.S. Application Data

(60) Provisional application No. 60/730,095, filed on Oct. 25, 2005.

(51) Int. Cl.
*G01N 30/86*    (2006.01)
(52) U.S. Cl.
USPC .......... 73/23.23; 73/23.35; 73/23.4; 700/266; 700/273; 702/194; 702/195
(58) Field of Classification Search
CPC .......... G01N 30/8624; G01N 30/8641; G01N 30/8651

USPC ......... 73/23.22, 23.23, 23.35, 23.4; 700/266, 700/273; 702/194, 195
See application file for complete search history.

(56) References Cited

U.S. PATENT DOCUMENTS

| | | | | |
|---|---|---|---|---|
| 4,837,726 | A * | 6/1989 | Hunkapiller | 702/32 |
| 5,592,402 | A * | 1/1997 | Beebe et al. | 703/6 |
| 5,674,388 | A * | 10/1997 | Anahara | 210/198.2 |
| 6,076,047 | A * | 6/2000 | Ito et al. | 702/32 |

(Continued)

FOREIGN PATENT DOCUMENTS

| | | |
|---|---|---|
| EP | 0222612 | 5/1987 |
| EP | 0969283 | 1/2000 |

(Continued)

OTHER PUBLICATIONS

Espacenet Bibliographic data for Japanese No. 2004506216, publication dated Feb. 26, 2004, Method and System for Identifying and Quantifying Chemical Components of a Mixture, abstract not available, patent corresponds to WO0213228.

(Continued)

*Primary Examiner* — Robert Clemente
(74) *Attorney, Agent, or Firm* — Muirhead and Saturnelli, LLC

(57) ABSTRACT

An apparatus and a method of chemical analysis entail acquiring a chromatogram, median filtering the chromatogram to produce a model baseline, smoothing the model baseline to reduce noise, and subtracting the smoothed model baseline from the acquired chromatogram to produce a modified chromatogram having a substantially flat baseline.

21 Claims, 6 Drawing Sheets

(56) References Cited

U.S. PATENT DOCUMENTS

| | | | |
|---|---|---|---|
| 6,112,161 | A * | 8/2000 | Dryden et al. .................. 702/85 |
| 6,314,374 | B1 * | 11/2001 | Ito et al. .......................... 702/32 |
| 6,427,526 | B1 * | 8/2002 | Davison et al. .............. 73/61.55 |
| 6,529,836 | B2 * | 3/2003 | Ito et al. .......................... 702/32 |
| 6,675,107 | B2 * | 1/2004 | Ito et al. .......................... 702/32 |
| 6,743,364 | B2 * | 6/2004 | van der Greef .............. 210/656 |
| 6,787,761 | B2 | 9/2004 | Hastings |
| 6,856,917 | B2 * | 2/2005 | Ito et al. .......................... 702/32 |
| 6,936,814 | B2 * | 8/2005 | Hastings ...................... 250/282 |
| 7,056,434 | B2 * | 6/2006 | van der Greef et al. ... 210/198.2 |
| 7,253,404 | B2 * | 8/2007 | Hastings ...................... 250/282 |
| 7,645,984 | B2 * | 1/2010 | Gorenstein et al. ........... 250/281 |
| 7,917,301 | B1 * | 3/2011 | Yip ................................. 702/20 |
| 8,017,908 | B2 * | 9/2011 | Gorenstein et al. ........... 250/282 |
| 2005/0109928 | A1 | 5/2005 | Hastings |

FOREIGN PATENT DOCUMENTS

| | | |
|---|---|---|
| GB | 2329475 | 3/1999 |
| JP | 62-32360 A | 2/1987 |
| JP | 62032360 | 2/1987 |
| JP | 62-127667 A | 6/1987 |
| JP | 63-88443 A | 4/1988 |
| JP | 63088443 | 4/1988 |
| JP | 07-270387 A | 10/1995 |
| JP | 10-339727 A | 12/1998 |
| JP | 10339727 | 12/1998 |
| JP | 11-153588 | 6/1999 |
| JP | 11153588 | 8/1999 |
| JP | 2004-506216 A | 2/2004 |
| WO | 0048023 | 8/2000 |
| WO | 0213228 | 2/2002 |

OTHER PUBLICATIONS

Espacenet Bibliographic data for Japanese No. JP62127667, publication date 1987-006-09, Method and Device for Correcting Data for Analysis From Chromatography Detector, Etc., abstract not available, patent corresponds to EP0222612.

Translation of Notice of Rejection for Japanese Patent Application No. 2008-538154, mailing date Jul. 19, 2011.

Moore et al; Median Filtering for Removal of Low-Frequency Background Drift, Anal. Chem. 1993, vol. 65, pp. 188-191.

Swartz, Michael; Ultra Performance Liquid Chromatography (UPLC): An Introduction; 8 Separation Science Redefined May 2005; www.chromatographyonline.com.

David C. Stone, Application of median filtering to noisy data, Canadian Journal of Chemistry, 1995, pp. 1573-1581, vol. 73, Canada.

Moore et al, Median Filtering for Removal of Low-Frequency Background Drift, Analytical Chemistry, 1993, pp. 188-191, vol. 65, American Chemical Society.

Japanese Application No. 2008-538154, Office Action dated May 22, 2012.

Hastings, et al., "New Algorithms for processing and peak detection in liquid chromatography/mass spectrometry data," Rapid Communication in Mass Spectrometry, 2002, vol. 16, No. 5, pp. 462-467.

* cited by examiner

BASELINE MODELING IN CHROMATOGRAPHY

CROSS-REFERENCE TO RELATED APPLICATIONS

This application claims benefit of and priority to U.S. Provisional Patent Application Ser. No. 60/730,095, filed Oct. 25, 2006, the entirety of which is incorporated herein by reference.

TECHNICAL FIELD

The invention relates to apparatus and methods that entail separation of chemical compounds.

BACKGROUND

Gas and liquid chromatography are commonly used in analytical and preparative chemistry. A typical chromatographic instrument utilizes a stationary inert porous material held in a column; a fluid containing a sample of interest is passed through the porous material. A typical liquid chromatography system includes a mobile-phase pump, a sample injector, a column, and a detector. The pump propels the mobile-phase fluid along a pathway that passes through the injector, column, and detector. The injector introduces a sample into the mobile-phase fluid prior to entry of the fluid into the column.

Distinct chemical compounds contained in the fluid often have distinct affinities for the medium held in the column. Consequently, as the fluid moves through the chromatographic column, various chemical compounds are delayed in their transit through the column by varying amounts of time in response to their interaction with the stationary porous material in the column. As a result, as the compounds are carried through the medium, the compounds separate into bands which elute from the column at different times.

Thus, the different chemical compounds in a sample solution separate out as individual concentration peaks as the fluid elutes from the column. The various separated chemicals can be detected by, for example, a refractometer, an absorbtometer, a mass spectrometer, or some other detecting device into which the fluid flows upon leaving the chromatographic column.

An ideal chromatographic signal, or chromatogram, has well-resolved peaks sitting on a baseline response that is a constant with low noise. Commonly, chromatograms are less-than ideal and contain, for example, fused peaks and a noisy baseline that has a slope and/or a curvature.

Some problems in the analysis of liquid-chromatography data relate to absorbance detection of separations during rapid solvent-gradient changes, where the change in mobile phase composition causes a curvature or slope of a chromatogram's baseline. A baseline slope or curvature can introduce difficulty in displaying very small peaks across a full chromatogram.

In general, visualization of small peaks requires expansion of the vertical (e.g., absorbance) scale. Unfortunately, baseline curvature at times renders such visualization difficult. An analyst may, for example, adjust the vertical scale so the whole of the vertical extent of the curved baseline is visible, leaving small peaks too small to see clearly. Alternatively, the analyst may, for example, expand the vertical so that one group of adjoining peaks is well-visualized, but other peaks may then reside above or below the vertical boundaries of the viewing region.

Fast chromatography systems, in particular, can experience difficulty due to baseline curvature or slope. For example, a change in mobile phase composition that causes a curvature or slope of a chromatogram's baseline may occur in fast, high resolution, very high pressure (greater than 5 kpsi, for example) reversed-phase separations; such sample separations require, for example, as little as 1 to 5 minutes to complete. During this time, the mobile phase ramps from, for example, nearly pure water to nearly pure acetonitrile. Variations in the baseline slope or curvature that are related to the change in a mobile phase composition may become more significant and apparent with the compression of a time axis that is associated with short duration separations.

Ideally, in some systems, such gradient effects are reduced, for example, through flowcell and/or optical designs. Typical strategies applied to conventional flowcells reduce gradient-induced refractive index effects by preventing rays that strike the inner walls of a flowcell from reaching a detector.

These solutions, however, generally cannot guarantee a flat baseline during a rapid gradient for both diode array and tunable single wavelength UV-visible absorbance detectors, particularly when light guiding flowcells are employed. Moreover, these solutions generally are not applicable to high peak capacity chromatography systems that utilize smaller volume flowcells while providing a long path length and high optical throughput, characteristics typically required for a high signal-to-noise measurement.

One alternative prior approach to the removal of baseline curvature or slope is suitable only for multi-wavelength detectors, such as photodiode array-based detectors. In this approach, a band of wavelengths is designated as a reference, where it is assumed that the analytes of interest do not absorb. As the separation progresses, absorbances at the analytical wavelengths are adjusted for changes in absorbance at the reference wavelength. This approach is preferably applied only when the baseline effects are the same at all wavelengths, a condition often not met using light guiding flowcells. Serious errors arise if any of the eluting compounds absorb at the reference wavelength. Moreover, noise from the reference wavelengths is added to the noise on the analytical signal.

SUMMARY

The invention arises from the realization that curvature and/or slope (such as shift and/or drift) is removed from a chromatogram with reduced impact on interpretation of chromatographic peak data by utilizing a smoothed baseline derived, in part, through use of a median filter. Moreover, the use of compression and decompression during data processing can reduce the computation time required to obtain a smoothed median-filter-derived baseline model. Features of the invention are particularly suited to mitigate problems that arise in liquid chromatography systems that utilize high fluidic pressures and detectors based on light-guided flow cells.

Thus, some embodiments of the invention provide a reduction in the curvature and/or slope of the baseline of a chromatogram with minimal impact on the meaningful data that can be extracted from peaks in the chromatogram. Moreover, some embodiments of the invention provide real-time background modeling, parallel implementation of detector channels, enhanced computational efficiency, and/or rules for the handling edge effects during chromatogram analysis.

Accordingly, in one illustrative embodiment, the invention features a method of chemical analysis. The method includes acquiring a chromatogram, applying a median filter to the chromatogram to provide a first approximate baseline. Typically, the chromatogram will have data points, each associated with a value of retention time and one or more values of magnitude such as absorbance values provided by a UV-based detector. The median filter removes chromatographic peak(s) to produce the first baseline approximation. The baseline approximation is then smoothed to reduce a noise component. Subtracting the smoothed baseline model from the chromatogram removes the baseline slope and/or curvature from the chromatogram, and thus provides a modified chromatogram having the chromatographic peak(s) and a substantially flat baseline.

Prior to filtering, the data of the chromatogram, after or during collection, are compressed. Decompression of data then optionally occurs after smoothing of the baseline approximation and prior to the subtraction of the model baseline from the original chromatogram. In some alternative implementations, compression and decompression are used to speed processing and reduce computation time while having little or no effect on a modified chromatogram otherwise obtained.

In some embodiments, a median filter is applied to a running portion of a chromatogram to construct a new baseline. In some of these embodiments, a first approximate baseline, obtained through use of the median filter, is smoothed by fitting a low-order polynomial, such as a quadratic polynomial, to a running portion of the first approximate baseline. The smoothed baseline may then be subtracted from the original chromatogram to produce a modified chromatogram having a substantially flat baseline. In some cases, proper choice of filter parameters of a median filter and/or a smoothing filter provides no significant alteration of observable retention time, area, and/or height of eluting peaks. In some embodiments that display a chromatogram in real-time, i.e., as the data is collected, the modified chromatogram, with baseline correction, is displayed with a delay of an amount of time related to filter widths.

In another illustrative embodiment, the invention features an apparatus for chemical analyses. The apparatus includes a control unit that is configured to implement, for example, one of the above-described methods.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The word "chromatography" and the like herein refer to equipment and/or methods used in the separation of chemical compounds. Chromatographic equipment typically moves fluids and/or ions under pressure and/or electrical and/or magnetic forces. The word "chromatogram," depending on context, herein refers to data or a representation of data derived by chromatographic means. A chromatogram can include a set of data points, each of which is composed of two or more values; one, of these values is often a chromatographic retention time value, and the remaining value(s) are typically associated with values of intensity or magnitude, which in turn correspond to quantities or concentrations of components of a sample.

The invention supports the generation and analysis of chromatographic data. Some embodiments of the invention involve instruments that include a single module that separates sample compounds while other embodiments involve multiple modules. For example, principles of the invention are applicable to liquid chromatography apparatus as well as to apparatus that include both liquid chromatography and mass spectrometry modules. In some multi-module-based embodiments; a chromatographic module is placed in fluidic communication with a mass-spectrometric module through use of an appropriate interface, such as an electrospray-ionization interface. Some appropriate interfaces at times create or maintain separated materials in an ionic form. A stream of sample fluid is typically vaporized, ionized, and delivered to an inlet orifice of a mass-spectrometry module.

Thus, some embodiments produce chromatograms composed of sets of data points, each of which is associated with a value of retention time (derived from the liquid chromatography module) and one or more values of intensity. The intensity values are obtained from observations of an eluent through use of, for example, an optical detector in a liquid-chromatography module and a mass analyzer in a mass-spectrometry module (typically a mass-to-charge ratio value.)

A typical chromatographic baseline has two prominent components: intrinsic high frequency noise, which reflects irreducible physical non-idealities of detectors; and baseline slope and curvature due to the chromatographic system, e.g., the interaction of a solvent phase with a flow cell. Some embodiments of the invention subtract the smooth curvature (e.g., due to the solvent interaction with a flow cell) while leaving the intrinsic high frequency detector noise unchanged and leaving the overlying chromatographic peaks unchanged.

Figure 1:
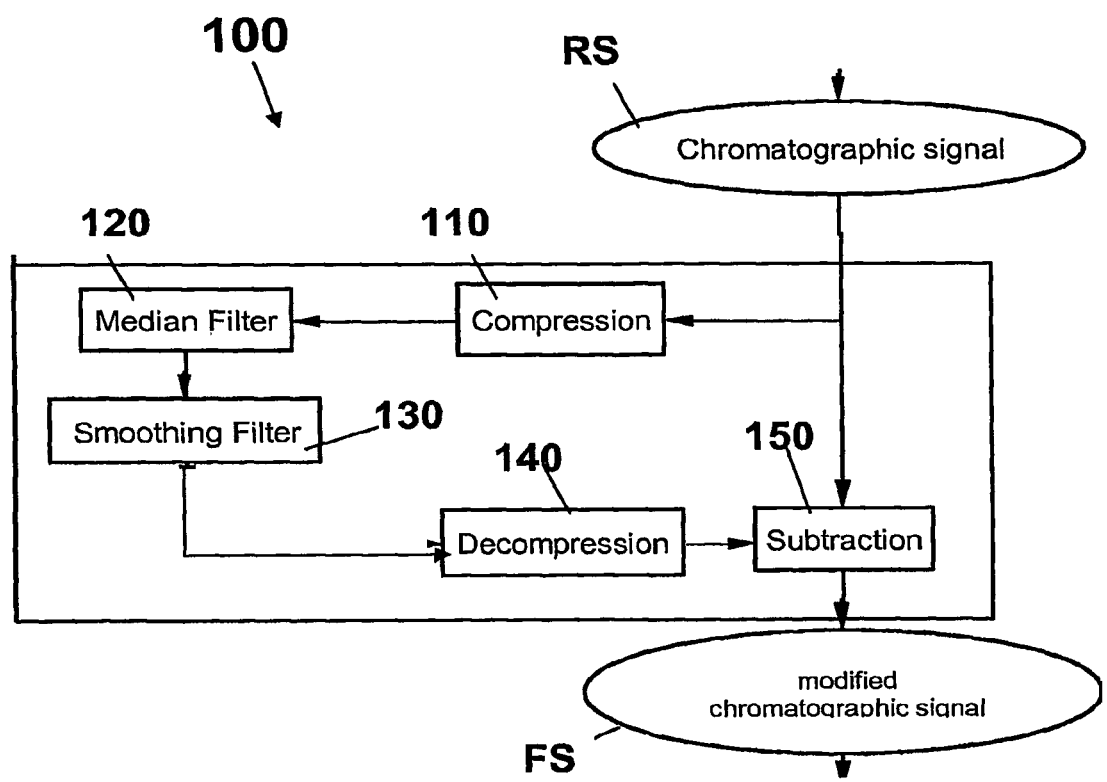
FIG. 1 is a flow diagram of a method of chemical analysis, in accordance with one embodiment of the invention.

FIG. 1 is a flow diagram of a method 100 of chemical analysis that supports removal of, for example, baseline drift and curvature from a chromatogram. The method 100 includes acquiring a chromatogram (illustrated at RS), applying 120 a median filter to the data points to provide a first approximate baseline. The median filter removes chromatographic peak(s) and/or at least one feature of curvature or slope from the chromatogram to produce the first approximate baseline. The first approximate baseline is then smoothed 130 to reduce a noise component of the first approximate baseline. Subtracting 150 the smoothed baseline from the chromatogram then provides a modified chromatogram (illustrated at FS) that includes the chromatographic peak(s) and has a substantially flat baseline. The acquisition of the chromatogram optionally occurs prior to or concurrently with applying 120 the median filter, smoothing 130 the derived baseline, and/or subtracting 150 the smoothed baseline from the chromatogram.

In some preferred embodiments, the data points are derived from a detector of a liquid chromatography module or instrument. Any suitable detector, including known detectors, may be utilized. Some suitable detectors include, for example, ultraviolet (UV) absorption detectors and evaporative light scattering detectors (ELSD), as known to one having ordinary skill in the liquid chromatography arts. In this case, the chromatogram's data points are each associated with a value of retention time and one or more values of magnitude such as absorbance values provided by a UV-based detector. Thus, though the following description, for convenience, is directed to examples involving UV absorbance detection, one having ordinary skill will recognize that alternative detectors are employable in alternative implementations of the invention.

Some embodiments advantageously generate a chromatography signal at a relatively high pressure (e.g., at pressures of 1 to 2 kpsi, up to 5 kpsi, or up to 10 kpsi, or greater) and by using a light guide-based detector having a flow cell with a relatively small volume (e.g., 0.5 μL to 15 μL.) The method 100 mitigates, for example, baseline curvature that may arise under these conditions.

In chromatograms derived from UV-absorbance detectors, baseline slope and/or curvature are typically determined by a combination of characteristics of the chromatographic apparatus, the separation method, and/or environmental conditions. These characteristics include, for example, solvent composition, flow-cell optics, photo-diode array response and/or electronics, and/or any thermal sensitivity that such systems at time exhibit. An analyst typically desires a flat chromatographic baseline having no measurable slope or curvature. In some cases, one may approach such ideal performance when thermally equilibrated detectors are employed with isocratic separations.

As understood by one having ordinary skill, some detectors utilizing light-guided flow cells ("LGFC") provide extremely low detector noise. Interaction with a gradient separation often causes, however, an undesirably curved baseline. Even if the baseline curvature is shallow enough to have little effect on interpretation of key characteristics of chromatographic peaks, such as retention time, peak height area or width, curvature is often visually distracting. The removal or reduction of such curvature often enhances the visualization and interpretation of chromatograms.

A median filter that is suitable for the step 120 is optionally viewed as an outlier filter that replaces a collection of data points that have intensity values far from true baseline values with a data point that is representative of a true baseline. Chromatographic peak(s) are thus optionally treatable as outlier(s); in effect, the step of applying 120 the median filter replaces the peak(s) with data points derived from portion(s) of the baseline that neighboring the peak(s) in the chromatogram.

The smoothing step 130 smoothes the first approximation to the baseline provided by the median filtering 120 step. Smoothing 130 optionally substantially eliminates high-frequency noise from the baseline, which otherwise would have a detrimental effect on the modified signal after subtracting 150. Smoothing 130 is optionally accomplished through use of any suitable filter, including known filters, such as filters based on use of a polynomial. As described below, one example of a suitable smoothing filter utilizes an apodized Savitzky-Golay $2^{nd}$-order polynomial. Savitzky-Golay polynomial smoothing filters are known to one having ordinary skill in the signal processing arts.

The presence of high-frequency noise in a model of a chromatogram's baseline has the potential to change the noise properties of the chromatogram after modification due to background subtraction; thus, such noise potentially affects observed characteristics of peaks in the chromatogram.

Baseline noise is typically an irreducible property of any detector and generally always present at some level in a chromatogram. Baseline noise arises from non-ideal properties that are intrinsic to detectors. In ultraviolet/visible (UV/Vis) detectors, noise typically includes shot noise and/or Johnson thermal noise having Gaussian statistics. In mass spectrometers, noise typically includes counting noise having Poisson statistics. Baseline noise is typically dominated by high frequency components, i.e. variations in amplitude occur many times during the width of a chromatographic peak.

Subtraction of a median filtered, smoothed model baseline from the original chromatogram in some embodiments of the invention neither increases nor reduces high frequency baseline noise. Thus, the model baseline contains only longer term underlying slope and curvature.

It is desirable to subtract a smoothed baseline to leave unchanged the chromatogram's underlying high frequency noise. A statistical characterization of a peak is then unchanged as the result of the model baseline subtraction. For example, measures of high-frequency baseline noise are unchanged.

When some methods of the invention are applied to a chromatogram that has no substantial baseline slope or drift, the modified chromatogram is substantially unchanged relative to the original chromatogram. For example, the peak properties of height, area, and width are unchanged, as well as the underlying high-frequency baseline noise.

By removing part or all of the high-frequency model baseline noise through smoothing 130 of the approximate baseline, the baseline that remains in a modified chromatogram—after subtracting 150 the smooth baseline from the original chromatogram—is desirably close to a straight line, but still has the same pattern of underlying high frequency baseline noise as was present in the original chromatogram. The subtraction 150 of a smooth model baseline from a chromatographic signal then leaves peak parameters and the underlying baseline noise of the modified chromatogram substantially unchanged.

Filter Window Widths—In some alternative implementations, the method 100 utilizes a median filter and a smoothing filter, for steps 120 and 130, having window widths that are pre-selected or variable in association with a range of retention time values. In these implementations, the behavior of the median filter (see step 120) and the behavior of the smoothing filter (see step 130) are controlled, in part, through use of adjustable parameters corresponding to the widths of the windows. These parameters are selected in any suitable way, such as two alternative ways described next.

As a first alternative, the width of the median filter window is set to at least twice the width of a chromatographic peak, and the width of the smoothing filter window is set to at least four times this peak width. The width of a chromatographic peak, in turn, is optionally expressed in terms of a number of sequential data points. Alternatively, for example, the peak width is expressed as a width in time; the window width in terms of number of data points then corresponds to the width in time units multiplied by the detectors sampling rate. Preferably, in some cases, the peak width is based on the widest peak and/or is equated to the full width at 5% of the peak height. Other suitable measures of peak width, as known to one having ordinary skill, are optionally utilized.

Generally, the median filter suitably removes chromatographic peaks if a sufficient portion of peak-free baseline resides within a window width. The smoothing filter is optionally selected to remove essentially all high-frequency noise from the approximate baseline and produce an essentially smooth curve that corresponds to the underlying, curved, chromatographic baseline. Over the width of the peak, this smooth curve is essentially linear in nature.

As a second alternative, the window widths of the filters are not determined in response to a peak width; rather the widths are associated with a chromatographic run time. For example, the widths are specified as a fraction of a chromatographic run time, in terms of, for example, sample data points. Suitably, for example, the width of the median filter window is approximately 10% of the run time, and the width of the smoothing filter window is approximately 20% of run time. These window widths are suitable where, for example, chromatographic peak widths are 5% or less of a run time, or where the peak capacity of a separation is 20:1 or greater. These values of filter window widths are large enough to accommodate most gradient separations, and narrow enough to yield a model baseline that substantially tracks the curvature of an underlying baseline of a chromatogram. One may suitably utilize the width of the expected broadest peak of a chromatogram in the determination of the window widths of the filters.

Rules for window width selection are optionally hard-coded in a data analysis component of a chemical processing system. Thus, a user (or system components) are optionally freed from selecting filter window widths.

In some embodiments, a median filter is a moving median filter. The "rank" r of the moving median filter optionally corresponds to the half-width of the filter window. That is, $$W = 1 + 2r$$

where W is the median filter width in number of data points, and r is the half-width.

The median filter is applied to successive points in the chromatogram, replacing each point with a new value, as provided by the filter; each filtered point is replaced with a point having a median intensity of the points within a window centered on the point to be filtered. The median of a set of points is the midpoint of the set (or other suitable definition), where equal numbers of points in the set have values greater than or less than the midpoint.

Regarding a window width, it is convenient to require a window to contain an odd number of data points. Thus, in some embodiments, a half window width, defined as $H = (W-1)/2$, is an even number.

In one real-time implementation of the method 100, when the $N^{th}$ point is acquired, the median filter outputs the median filtered value of $(N-H)^{th}$ point.

As described above, in some implementations, the window width of the median filter is desirably at least twice the width of the broadest peak, and the width of the smoothing filter is desirably at least four times the width of the broadest peak. In many cases, filters whose window widths are wider than these values will leave peak parameters intact. Filters that have narrower window widths than these values will generally lead to distorted peaks.

Figure 2A:
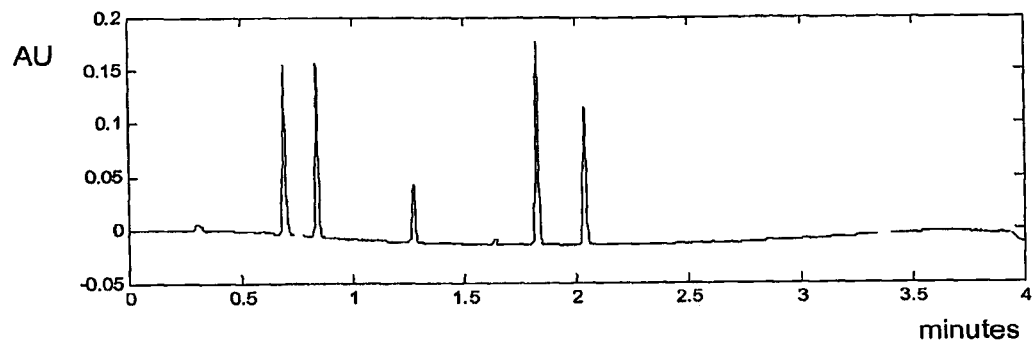
FIG. 2A is a graph of an example chromatogram.
Figure 2B:
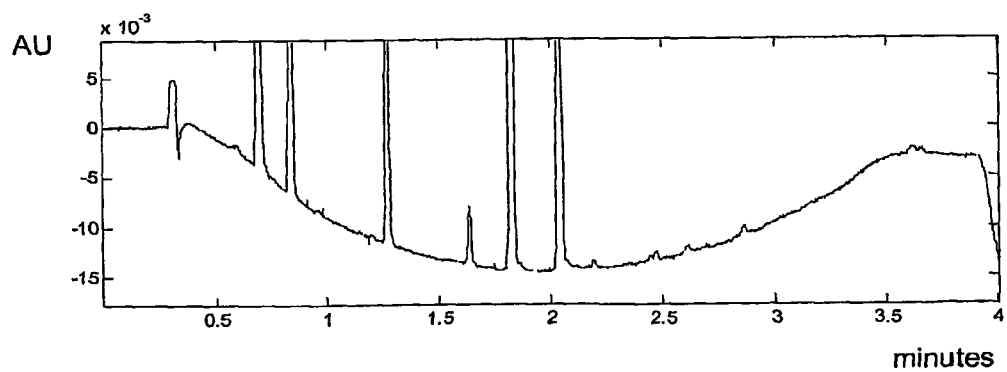
FIG. 2B is a graph of the chromatogram of FIG. 2A, though having an expanded vertical axis.

Next referring to FIGS. 2A, 2B, 3A, 3B, 4A and 4B, an example of the behavior of median and smoothing filters is described. FIG. 2A is a graph of an example chromatogram, as-collected (vertical axis corresponding to absorbance units (AU) derived from a UV detector and horizontal axis corresponding to the retention time of a sample run.) FIG. 2B is the same chromatogram though graphed with an expanded vertical axis to highlight the curvature of the example chromatogram.

Figure 3A:
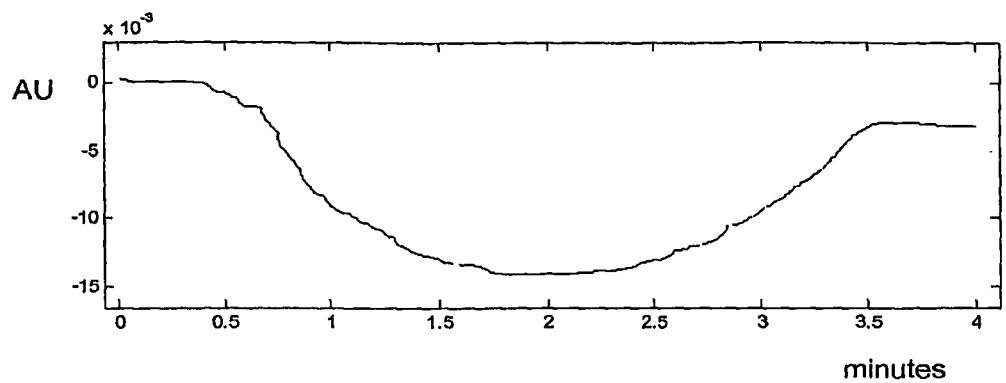
FIG. 3A is a graph of a first approximate baseline obtained from the chromatogram of FIG. 2B, in accordance with one embodiment of the invention.
Figure 3B:
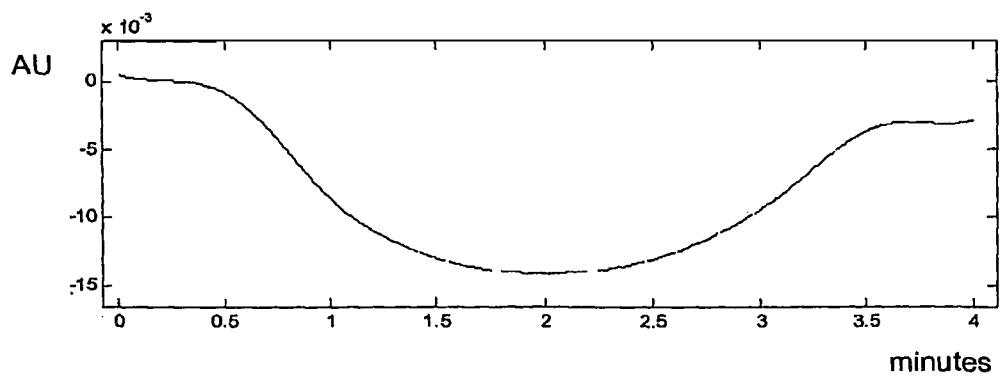
FIG. 3B is a graph of a smoothed model baseline derived by smoothing the baseline of FIG. 3A.

FIGS. 3A and 3B illustrate the development of a median-filtered, smoothed model baseline from the chromatogram of FIG. 2B. FIG. 3A is a graph of an approximate baseline obtained from the chromatogram of FIG. 2B by median filtering (see step 120.) FIG. 3B is a graph of the smoothed approximate baseline obtained by applying a smoothing filter (see step 130) to the approximate baseline of FIG. 3A.

FIG. 3B illustrates the removal of high-frequency noise from the median filtered, approximate baseline of FIG. 3A. In this example, the smoothing filter has removed high-frequency noise passed by the median filter, leaving a model smooth baseline, substantially free of detector noise artifacts.

Figure 4A:
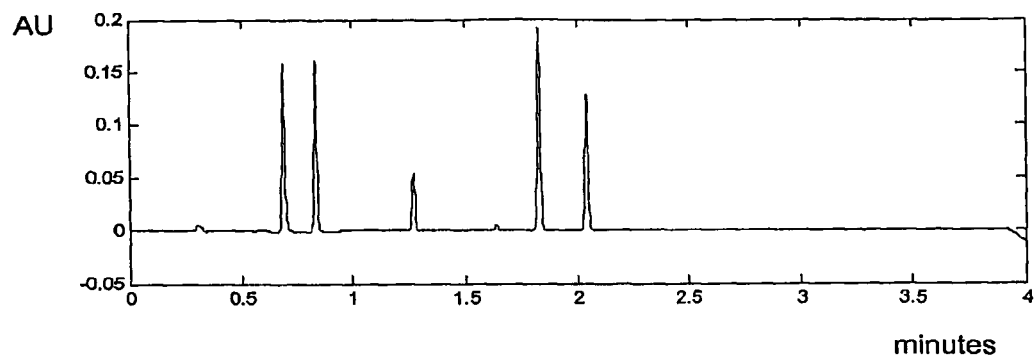
FIG. 4A is a graph of a modified chromatogram obtained by subtracting the smoothed model baseline of FIG. 3B from the acquired chromatogram of FIGS. 2A and 2B.
Figure 4B:
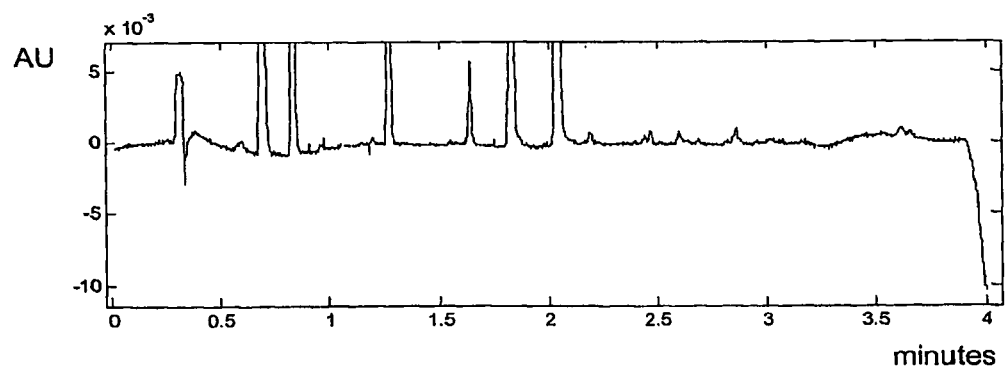
FIG. 4B is a graph of the modified chromatogram of FIG. 4A, though having an expanded vertical axis.

FIG. 4A is a graph of the modified chromatogram, after subtracting 150 the smoothed model baseline of FIG. 3B from the acquired chromatogram of FIGS. 2A and 2B (scale same as FIG. 2A.) FIG. 4B is a graph of the same modified chromatogram though graphed with an expanded vertical axis, similar to that of FIG. 2B and FIG. 3B, to highlight the removal of curvature from the acquired chromatogram (compare to FIG. 2B.)

Figure 5:
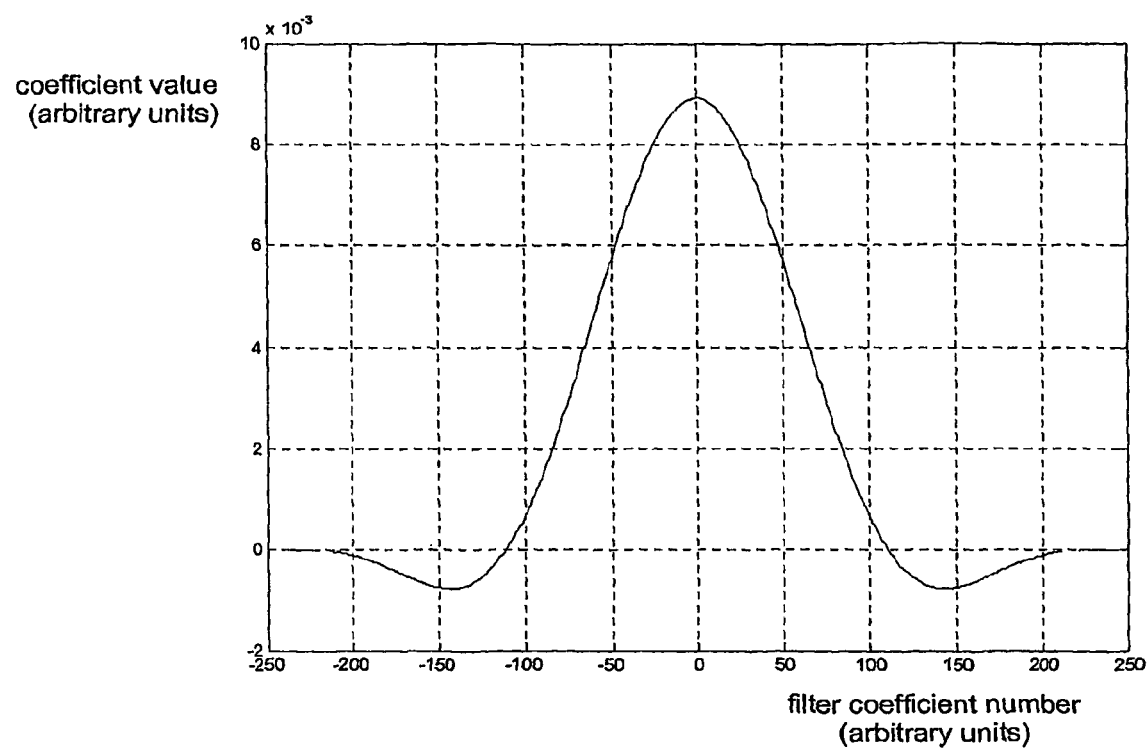
FIG. 5 is a graph of an illustrative apodized Savitzky-Golay $2^{nd}$-order polynomial-based filter.

Next referring to FIG. 5, the apodized Savitzky-Golay $2^{nd}$-order polynomial smoothing filter, of the present example, is described in more detail. The smoothing filter is applied (see step 120) to successive points in the approximate baseline, replacing each point with a new value. In this example, each point is replaced with a weighted average of the points within a window centered on the point to be smoothed. The weighting values applied to each point correspond to coefficients of the smoothing filter. For some suitable smoothing filters, such as that used in the present example, these values sum to unity.

One obtains an apodized Savitzky-Golay filter by applying a cosinusoidal-shaped weighting function to the data when fitting the data to a $2^{nd}$-order polynomial curve. The cosinusoidal-shaped weighting function gives the highest weight in the center of the fitting window, and the weight value falls to zero symmetrically at the filter boundaries. The present example conveniently utilizes a window width having an odd number of points.

FIG. 5 is a graph that illustrates the apodized Savitzky-Golay, $2^{nd}$-order polynomial of the present example. The values of the filter coefficients (which sum to 1) are plotted against filter numbers (arbitrary units); in this example, there are 483 filter coefficients. As for a typical moving average filter, each output data point is obtained by applying the filter to a window of data points, each data point in association with a corresponding one of the filter coefficients. Each output data point is obtained by multiplying coefficients of the filter with the corresponding data point values and then summing the products. The filter coefficients are then stepped one sample point at a time, producing a new filter output at each step.

Oversampling of the chromatogram's data points is utilized in this example. Thus, oversampling, as known in the art, is used in the present example to provide 483 oversampled data points in the window.

It is a known characteristic of quadratic polynomial filters that each output point of such a filter gives a value that is equivalently obtained by fitting a quadratic polynomial to a window of data corresponding to the filter width. The filter output is equivalent to the fitted value at the center of the filter window.

An apodized Savizky-Golay filter, of one embodiment of the invention, has coefficients that provide results that are equivalent to what would be obtained from a weighted leastsquares fit to a data window. The weighting (apodizing) function of this embodiment is a cosinusoid that has a maximum in the center and falls smoothly to zero at the filter ends. The result of the weighting (apodization) is that the filter coefficients have attenuated values near the ends, which assist in further removing high-frequency ripple from a median filter-derived baseline.

Data Compression—The optional compression and decompression steps 110, 140 respectively precede and follow the filtering steps 120, 130. As described next, the compression and decompression steps 110, 140, in some cases, reduce the operation count, thus reducing the duration of a computation.

In one illustrative embodiment, the peak widths are used to determine most or all data acquisition parameters, which include sampling rate, and filter width parameters. Suitably, for example, the sampling rate is selected to provide approximately 15 data points across a peak width (measured, for example, as full-width at 5% of a peak height.) In this example, the median filter is selected to encompass at least 30 data points, and the smoothing filter is selected to encompass at least 60 data points.

An analyst optionally chooses to acquire data at significantly higher sampling rates, resulting in significantly more data points collected across a peak. For example, if 150 data points are collected across a peak, one suitable implementation would require 300 points for the median filter width and 600 points for the smoothing filter width.

Generally, the number of multiplication operations required to implement the smoothing step 130, in this example, increases as the square of the sampling rate. More points must be smoothed, and more points are processed to obtain each smoothed point. The higher sampling rate does not necessarily increase the accuracy of the model baseline, and may thus cause an unnecessary computational burden.

To ease this burden, in one example of a compression step 110, a number of data points corresponding to a compression factor, F, are averaged to produce a decimated chromatogram from the acquired chromatographic signal. Thus, for example, 10 data points are combined via averaging to produce a smaller (compressed) chromatogram, from which the model baseline is obtained (via steps 120, 130.) The model baseline is then decompressed 140 via linear interpolation to then allow point-by-point subtraction 150.

In an example based on run time rather than reliance on information about a peak width, one determines a maximum peak capacity and selects as a conservative target rate 20 data points per peak. Rather than a value of 10, the compression factor, F, in this example is:

$$F = \text{ceil}\left(\frac{N}{C_m S_t}\right)$$

where N is the total number of data points per chromatogram, $C_m$ is the maximum peak capacity, $S_t$ is the target sampling rate, and the cell function, as known, rounds upward to an integer value. For illustration, $C_m=200$, and $S_t=20$.

Real-Time Analysis and Presentation—As mentioned, a median filtering step 120 is applied as a post-processing filter to data after acquisition or is applied to data in real-time, as the data are collected. If a chromatogram is displayed in real-time, as the data are collected, the modified chromatogram, with baseline correction, is generally delayed by an amount related to filter window widths.

In one example of a real-time implementation, each data point derived from detector(s) is stored, and included in a window of data that is then median filtered. Each new output data point produced by median filtering is stored and optionally then used by a smoothing filter. Each output data point, after application of a smoothing filter, is then optionally subtracted from the corresponding original raw data point to produce a modified chromatogram data point.

In a steady state, data points of a modified chromatogram are produced at the same rate that raw data points of the chromatogram are received. The widths of filter windows determines a time delay between the timing of the input and output chromatograms. In general, the delay is one half the sum of the filter widths.

As mentioned, a baseline-corrected chromatogram is obtained, for example, by subtracting the model smoothed baseline point-by-point from the original chromatogram. Thus, in the example real-time implementation, the subtraction step 150 optionally outputs the modified value(s) of the original $N^{th}$ data point upon determination of the $N^{th}$ data point of the model baseline.

Detectors—Various embodiments of the invention utilize data obtained from one or more suitable optical detectors, including known optical detectors, such as a photodiode array (PDA) detector, a tunable UV (TUV) detector, and or an ELSD. In some implementations, the chromatogram's data points each include magnitude values associated with parallel streams of data. For example, one embodiment of the invention includes an array type detector, such as a 512-element PDA-based detector. The time course of each stream of data derived from each pixel in a PDA is optionally treated independently. Thus, the curvature of each baseline is removed independently of the others.

One suitable TUV detector is a dual wavelength ultraviolet/visible (UV/Vis) detector that utilizes a light-guiding flow cell and supports data rates up to 80 Hz or more. Such a TUV or other detector optionally provides a single channel of data.

As known to one having ordinary skill in the chromatographic arts, an ELSD is helpful for detection of compounds that exhibit little to no UV/Vis response and do not ionize well for mass spectrometry. Such compounds include, for example, sugars, antibiotics, antivirals, biomolecules, and natural products.

Handling of Edge Effects—Some embodiments of the invention mitigate the potential problem of filter edge effects. For example, in embodiments described above, both the median filter and the smoothing filter take as input a window of data points centered on the data point to be filtered. The first and last data points, and neighboring data points in some cases, of an acquired chromatogram are not filtered unless a special rule is invoked. One suitable rule is to augment the chromatogram by adding data points before the first data point and data points after the last point, in sufficient number to allow the operation of the filters. For the median filter, the data points are augmented with $H_m$ data points, and, for the smoothing filter, the data points are augmented by $H_s$ data points.

To obtain points, $d_{-i}$, before the first acquired point, $d_o$, one suitable rule is:

$$d_{-i} = d_o - (d_i - d_o) = 2d_o - d_i$$

where $d_o$ is the first point in the chromatogram, $d_i$ is the $i^{th}$ point, and $d_{-i}$ is the reflected point.

Figure 6:
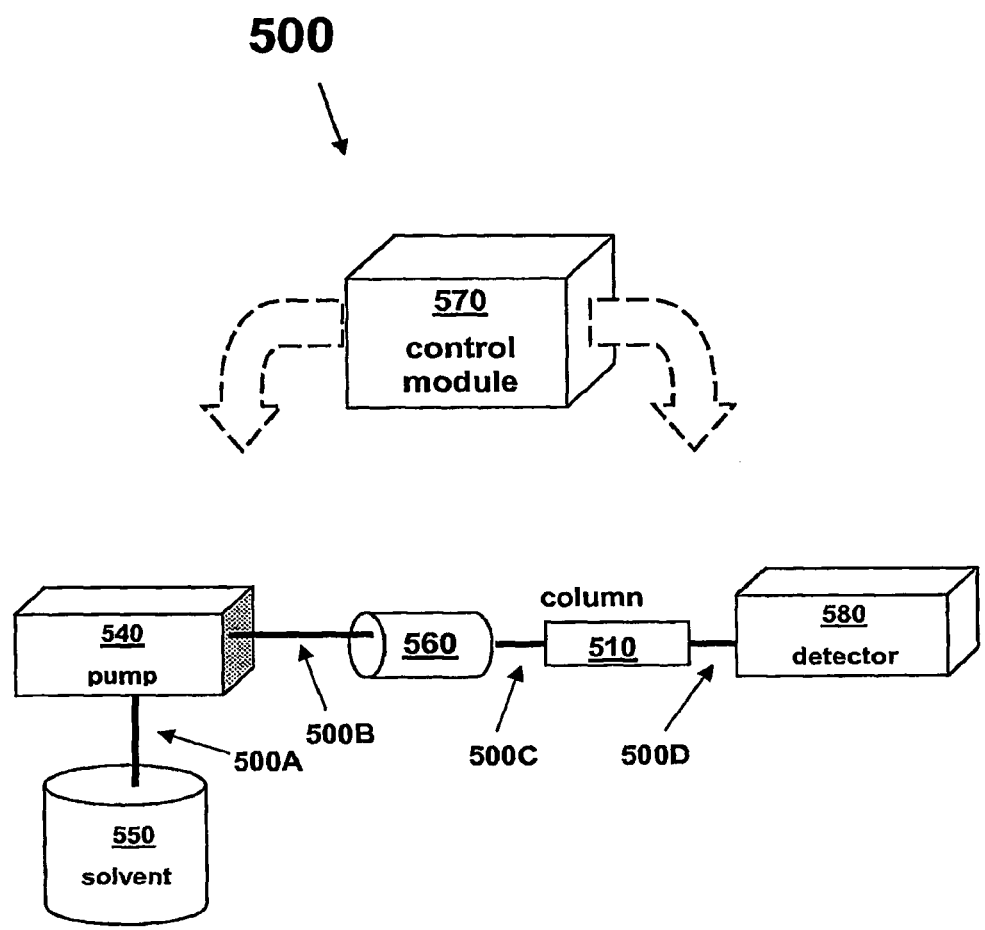
FIG. 6 is a block diagram of a high-pressure chromatography apparatus, in accordance with one embodiment of the invention.

Next referring to FIG. 6, some embodiments of the invention are chemical-processing systems such as chromatographic systems that include LC and/or MS modules. Some of these embodiments include a control unit. In some of these embodiments, the control unit is in data communication with other components of the system via wired and/or wireless means, such as those known in the data-communication arts. The control unit receives process data, for example, and provides control signals to other components, for example. The control unit includes and/or is in communication with storage component(s).

FIG. 6 is a block diagram of a high-pressure chromatography apparatus 500, in accordance with another alternative embodiment of the invention. The apparatus 500 includes a separation column 510, a solvent reservoir 550, a solvent pump 540, a sample injector 560, a detector 580, tubing 500A connecting the pump 540 to the reservoir 550, tubing 500B connecting the pump to the injector 560, tubing 500C connecting the column 510 to the injector 560, tubing 500D connecting the column 510 to the detector 580, and a control module 570.

The tubing 500B, 500C, 500D optionally has inner diameter(s) appropriate for nano-flow chromatography, for example, within a range of about 20 µm to about 40 µm. Each section of the tubing 500B, 500C, 500D optionally has a different inner diameter, as desired.

In a preferred implementation, the detector 580 utilizes a light-guided flow cell that accommodates relatively small volumes of fluid. One suitable detector is described in International Application Publication No. WO/2002/071029, titled "Fluorescence Detector Geometry," to Gilby, which is incorporated herein by reference.

In some alternative implementations, the apparatus 500 is based on a known high-pressure chromatographic instrument, though modified to implement features of the above-described methods. One suitable commercially available instrument is the nanoACQUITY UPLC™ System (available from Waters Corporation, Milford, Mass.)

The control module 570—including, for example, a personal computer or workstation—receives data and/or provides control signals via wired and/or wireless communications to, for example, the pump 540, the injector 560, and/or the detector 580. The control module 570 supports, for example, automation of sample analyses. The control module 570, in various alternative embodiments, includes software, firmware, and/or hardware (e.g., such as an application-specific integrated circuit), and includes, if desired, a user interface. Optionally, for example, one or more microprocessors implement software that enables the functions of the module 570. In some embodiments, the software is designed to run on general-purpose equipment and/or specialized processors dedicated to the functionality herein described.

The column 540 contains any suitable stationary medium. For example, the medium optionally contains any suitable medium for nano-flow chromatography, such as a particulate medium known to one of ordinary skill. Some suitable media include silica or hybrid sorbents having particle diameters in a range of approximately 1 µm to approximately 5 µm.

In some embodiments, a particulate medium includes hybrid particles, as found, for example, in the BEH Technology™ Acquity UPLC™ 1.7 µm columns (available from Waters Corporation, Milford, Mass.) Other embodiments include larger particles, such as 3 µm or 5 µm particles. Some of these embodiments involve trap columns. Suitable columns are up to 25 cm in length, or greater, and have inner diameters in a range of, for example 20 µm to 300 µm, for example, 75 µm, 100 µm or 150 µm.

The pump unit 540 is configured to provide nano-flow of solvent at pressures of at least approximately 5,000 psi or 10,000 psi or greater. The pump unit includes any suitable pump components, including known pump components, such as those found in Acquity HPLC™ liquid chromatography instruments (available from Waters Corporation, Milford, Mass.)

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

We claim:

1. A method of chemical analysis, comprising:
    acquiring a chromatogram associated with data points that each have a value of retention time and at least one value of magnitude;
    compressing the acquired chromatogram;
    removing at least one chromatographic peak from the compressed chromatogram by median filtering the data points to provide a model baseline;
    smoothing the model baseline to reduce a noise component of the model baseline;
    decompressing the smoothed model baseline; and
    subtracting the decompressed smoothed model baseline from the acquired chromatogram to produce a modified chromatogram having the at least one chromatographic peak and a substantially flat baseline.

2. The method of claim 1, wherein acquiring the chromatogram comprises collecting optical absorption data from a detector comprising a light-guided flow cell.

3. The method of claim 1, wherein smoothing comprises applying a smoothing filter.

4. The method of claim 3, wherein applying a smoothing filter comprises selecting a window width of the smoothing filter.

5. The method of claim 4, wherein the width is at least about four times a widest expected chromatographic peak width.

6. The method of claim 5, wherein the peak width is determined at about 5% peak height.

7. The method of claim 5, wherein the peak width is associated with about 20% of a sample run time.

8. The method of claim 3, wherein the smoothing filter comprises coefficients that implement a polynomial smoothing filter.

9. The method of claim 3, wherein applying the smoothing filter comprises augmenting filtered data points of the model baseline chromatogram to mitigate edge effects.

10. The method of claim 1, wherein the noise component comprises high-frequency noise.

11. The method of claim 1, wherein acquiring the chromatogram comprises collecting optical absorption data from a photodiode array-based detector.

12. The method of claim 1, wherein median filtering comprises mitigating edge effects.

13. The method of claim 12, wherein mitigating edge effects comprises augmenting the data points of the chromatogram.

14. The method of claim 1, wherein subtracting comprises point-by-point subtracting.

15. The method of claim 1, wherein subtracting occurs in real time.

16. The method of claim 1, wherein median filtering the data points comprises filtering during acquisition of the data points.

17. The method of claim 1, wherein median filtering the data points comprises filtering after acquiring all of the data points.

18. The method of claim 1, wherein said compressing includes averaging a number of data points corresponding to a compression factor F to produce a decimated chromatogram from the acquired chromatogram.

19. The method of claim 1, wherein said decompressing includes decompressing the smoothed model baseline via linear interpretation to then allow point-by-point subtraction.

20. An apparatus for chemical processing, comprising:
a chromatography module comprising a detector comprising a light-guided flow cell; and
a control unit, in communication with the detector, comprising at least one processor and at least one memory comprising a plurality of instructions stored thereon for:
acquiring a chromatogram associated with data points that each have a value of retention time and at least one value of magnitude derived from the detector,
compressing the acquired chromatogram,
removing at least one chromatographic peak from the compressed chromatogram by median filtering the data points to provide a model baseline,
smoothing the model baseline to reduce a noise component of the model baseline,
decompressing the smoothed model baseline, and
subtracting the decompressed smoothed model baseline from the acquired chromatogram to produce a modified chromatogram having the at least one chromatographic peak and a substantially flat baseline.

21. A non-transitory computer readable medium comprising code stored thereon for chemical analysis, the non-transitory computer readable medium comprising code for:
acquiring a chromatogram associated with data points that each have a value of retention time and at least one value of magnitude;
compressing the acquired chromatogram;
removing at least one chromatographic peak from the compressed chromatogram by median filtering the data points to provide a model baseline;
smoothing the model baseline to reduce a noise component of the model baseline;
decompressing the smoothed model baseline; and
subtracting the decompressed smoothed model baseline from the acquired chromatogram to produce a modified chromatogram having the at least one chromatographic peak and a substantially flat baseline.

* * * * *